United States Patent
Bonde

(10) Patent No.: US 9,468,751 B2
(45) Date of Patent: Oct. 18, 2016

(54) MEDICAL DEVICE ANCHORING APPARATUS

(71) Applicant: Medtronic, Inc., Minneapolis, MN (US)

(72) Inventor: Eric H. Bonde, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 322 days.

(21) Appl. No.: 13/795,458

(22) Filed: Mar. 12, 2013

(65) Prior Publication Data

US 2014/0155859 A1 Jun. 5, 2014

Related U.S. Application Data

(60) Provisional application No. 61/733,584, filed on Dec. 5, 2012.

(51) Int. Cl.
*A61N 1/05* (2006.01)
*A61B 19/00* (2006.01)
(Continued)

(52) U.S. Cl.
CPC ............ *A61N 1/0539* (2013.01); *A61M 25/04* (2013.01); *A61B 17/3468* (2013.01);
(Continued)

(58) Field of Classification Search
CPC ............ A61N 1/0539; A61N 1/0526–1/0536;
A61M 39/0247; A61M 2039/0273; A61M 2039/0279; A61M 2039/0288; A61M 2039/0666; A61M 2039/062; A61M 2039/066; A61M 2039/0673; A61M 2039/025; A61M 2039/0252–2039/0261; A61M 2039/0235; A61M 2039/027; A61M 2039/064; A61M 25/02; A61M 2025/0293; A61M 2025/0213; A61M 2025/024; A61M 2025/0246; A61M 2025/028; A61B 2019/208; A61B 2019/2211

USPC ........... 607/139, 116; 604/174, 288.03, 178, 604/167.04
See application file for complete search history.

(56) References Cited

U.S. PATENT DOCUMENTS

| 5,464,446 A | 11/1995 | Dreessen et al. |
| 5,843,150 A | 12/1998 | Dreessen et al. |

(Continued)

FOREIGN PATENT DOCUMENTS

| EP | 1016432 A2 | 7/2000 |
| GB | 2344054 | 5/2000 |

(Continued)

OTHER PUBLICATIONS

The International Search Report and The Written Opinion, PCT/US2013/073429, Jul. 24, 2014, 19 pages.

(Continued)

*Primary Examiner* — Christopher L Templeton
(74) *Attorney, Agent, or Firm* — Mueting, Raasch & Gebhardt, P.A.

(57) ABSTRACT

Methods and apparatus for anchoring an implanted elongate medical device in a body portal, for example, a stimulation lead in a cranial burr hole, employ a securing element attached to an upper surface of a plate member, and moveable relative thereto, from an open position, at which the device may be inserted into a slot of the plate member, and a closed position, at which an engagement surface of the securing element anchors the inserted device. The securing element may extend at angle, with respect to a plane of the plate member, in the open position, and rotating the securing element lifts the engagement surface into the closed position. A locking member preferably extends from an upper surface of the plate member, and, when a latching portion of the securing element moves into engagement with the locking member, the element is moved into the closed position and secured thereat.

12 Claims, 6 Drawing Sheets

(51) Int. Cl.
*A61M 25/04* (2006.01)
*A61M 25/02* (2006.01)
*A61B 17/34* (2006.01)
*A61N 1/36* (2006.01)
*A61M 5/00* (2006.01)

(52) U.S. Cl.
CPC .......... *A61B 17/3472* (2013.01); *A61B 90/11* (2016.02); *A61B 2017/347* (2013.01); *A61B 2034/301* (2016.02); *A61B 2034/302* (2016.02); *A61B 2090/103* (2016.02); *A61M 5/00* (2013.01); *A61M 2025/024* (2013.01); *A61N 1/36025* (2013.01); *A61N 2001/36039* (2013.01)

(56) References Cited

U.S. PATENT DOCUMENTS

| | | | |
|---|---|---|---|
| 5,865,842 | A | 2/1999 | Knuth et al. |
| 5,927,277 | A | 7/1999 | Baudino et al. |
| 5,954,687 | A | 9/1999 | Baudino |
| 6,044,304 | A | 3/2000 | Baudino |
| 6,134,477 | A | 10/2000 | Knuteson |
| 6,210,417 | B1 | 4/2001 | Baudino et al. |
| 6,214,016 | B1 | 4/2001 | Williams et al. |
| 6,321,104 | B1 | 11/2001 | Gielen et al. |
| 6,902,569 | B2 | 6/2005 | Parmer et al. |
| 7,033,326 | B1 | 4/2006 | Pianca et al. |
| 7,177,701 | B1 | 2/2007 | Pianca |
| 7,204,840 | B2 | 4/2007 | Skakoon et al. |
| 7,235,084 | B2 | 6/2007 | Skakoon et al. |
| 7,346,391 | B1* | 3/2008 | Osorio et al. .......... 607/2 |
| 7,421,297 | B2 | 9/2008 | Giftakis et al. |
| 7,580,756 | B2 | 8/2009 | Schulte et al. |
| 7,588,581 | B2 | 9/2009 | Solar et al. |
| 7,604,644 | B2 | 10/2009 | Schulte et al. |
| 7,604,655 | B2 | 10/2009 | Warnick |
| 7,637,915 | B2 | 12/2009 | Parmer et al. |
| 7,704,260 | B2 | 4/2010 | Skakoon et al. |
| 8,050,772 | B1* | 11/2011 | Daglow et al. ........ 607/116 |
| 8,738,151 | B2 | 5/2014 | Nelson |
| 2002/0052610 | A1* | 5/2002 | Skakoon et al. ....... 606/129 |
| 2005/0015128 | A1* | 1/2005 | Rezai et al. ........... 607/115 |
| 2005/0054985 | A1* | 3/2005 | Mogg ............ A61M 25/02 604/174 |
| 2005/0143800 | A1 | 6/2005 | Lando et al. |
| 2005/0182420 | A1* | 8/2005 | Schulte et al. ........ 606/130 |
| 2005/0182421 | A1 | 8/2005 | Schulte et al. |
| 2005/0182422 | A1 | 8/2005 | Schulte et al. |
| 2005/0182423 | A1 | 8/2005 | Schulte et al. |
| 2005/0182424 | A1 | 8/2005 | Schulte et al. |
| 2005/0182425 | A1 | 8/2005 | Schulte et al. |
| 2005/0182464 | A1 | 8/2005 | Schulte et al. |
| 2005/0192594 | A1* | 9/2005 | Skakoon et al. ....... 606/129 |
| 2007/0233158 | A1 | 10/2007 | Rodriguez |
| 2007/0249980 | A1 | 10/2007 | Carrez et al. |
| 2008/0017206 | A1 | 1/2008 | Becker et al. |
| 2008/0172068 | A1* | 7/2008 | Adams et al. ......... 606/130 |
| 2009/0088826 | A1* | 4/2009 | Bedenbaugh ......... 607/116 |
| 2009/0112327 | A1 | 4/2009 | Lane et al. |
| 2009/0118804 | A1 | 5/2009 | Moffitt et al. |
| 2009/0187149 | A1* | 7/2009 | Nelson .................. 604/175 |
| 2009/0259186 | A1* | 10/2009 | Smith et al. ........ 604/167.04 |
| 2010/0023100 | A1 | 1/2010 | Barker |
| 2010/0145357 | A1 | 6/2010 | Lane et al. |
| 2010/0280585 | A1 | 11/2010 | Appenrodt et al. |
| 2011/0238040 | A1 | 9/2011 | Johnson |
| 2012/0010626 | A1 | 1/2012 | Daglow et al. |
| 2012/0316628 | A1* | 12/2012 | Lopez .................... 607/116 |
| 2014/0155860 | A1 | 6/2014 | Behymer et al. |
| 2014/0155909 | A1 | 6/2014 | Bonde et al. |

FOREIGN PATENT DOCUMENTS

| | | |
|---|---|---|
| WO | 2005079903 A2 | 9/2005 |
| WO | 20060054691 A2 | 5/2008 |
| WO | 2009055746 A2 | 4/2009 |
| WO | 2014089360 A2 | 6/2014 |
| WO | 2014089366 A2 | 6/2014 |
| WO | 2014089371 A2 | 6/2014 |

OTHER PUBLICATIONS

Invitation to Pay Additional Fees and Communication Relating to the Results of the Partial International Search, PCT/US2013/073436, Apr. 10, 2014, 6 pages.
Invitation to Pay Additional Fees and Communication Relating to Results of the Partial International Search, PCT/US2013/073419, Apr. 9, 2014, 7 pages.
Guardian Cranial Burr Hole Cover System, Clinician's Manual, ANS, Apr. 2009.
The International Search Report and The Written Opinion, PCT/US2013/073419, Jul. 2, 2014, 19 pages.
U.S. Appl. No. 13/795,441; Office Action issued Jan. 29, 2015.
PCT Patent Application No. PCT/US2013/073419, filed Dec. 5, 2013; International Preliminary Report on Patentability issued Jun. 18, 2015; 12 pages.
PCT Patent Application No. PCT/US2013/073429, filed Dec. 5, 2013; International Preliminary Report on Patentability issued Jun. 18, 2015; 13 pages.
PCT Patent Application No. PCT/US2013/073429, filed Dec. 5, 2013; Invitation to Pay Additional Fees and Communication Relating to the Results of the Partial International Search issued Feb. 27, 2014, 6 pages.
PCT Patent Application No. PCT/US2013/073436, filed Dec. 5, 2013; International Search Report and Written Opinion issued Aug. 28, 2014; 16 pages.
PCT Patent Application No. PCT/US2013/073436, filed Dec. 5, 2013; International Preliminary Report on Patentability issued Jun. 18, 2015; 10 pages.
U.S. Appl. No. 13/795,441; Office Action issued May 26, 2015; 10 pages.
U.S. Appl. No. 13/795,441, filed Mar. 12, 2013, Bonde et al.
U.S. Appl. No. 13/795,490, filed Mar. 12, 2013, Behymer et al.
U.S. Appl. No. 13/795,441; Office Action issued Oct. 2, 2015; 6 pages.
U.S. Appl. No. 13/795,441; Office Action issued Dec. 9, 2015; 8 pages.
U.S. Appl. No. 13/795,441; Advisory Action issued Feb. 19, 2016; 3 pages.
U.S. Appl. No. 13/795,490; Office Action issued Sep. 18, 2015. 11 pages.
U.S. Appl. No. 13/795,490; Office Action issued Mar. 8, 2016. 11 pages.
Dictionary definition of "press fit" as provided by PTO with Mar. 8, 2016 Office Action in U.S. Appl. No. 13/795,490, [indicated by PTO as being retrieved on Mar. 2, 2016]. Retrieved from the Internet: <URL:http://dictionary.reference.com/browse/press-fit>, 2 pages.

* cited by examiner

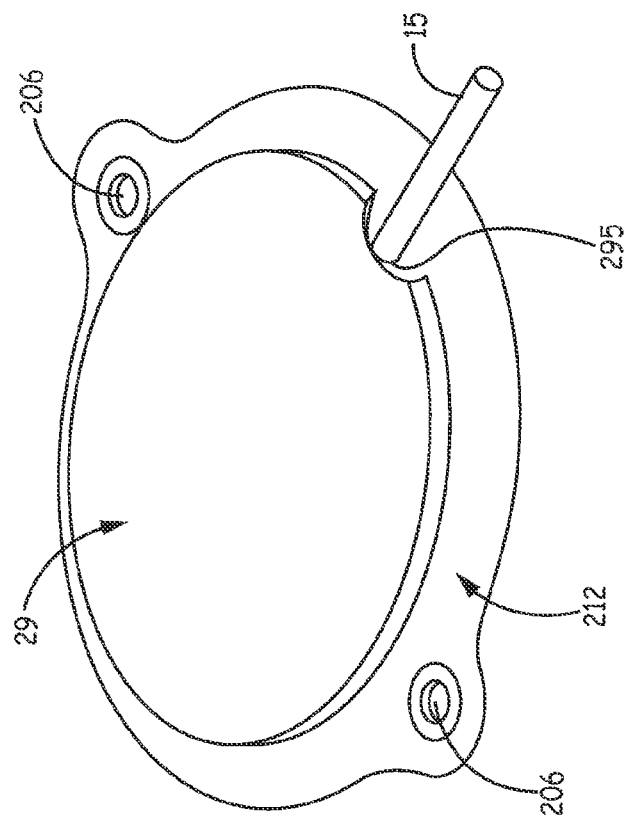
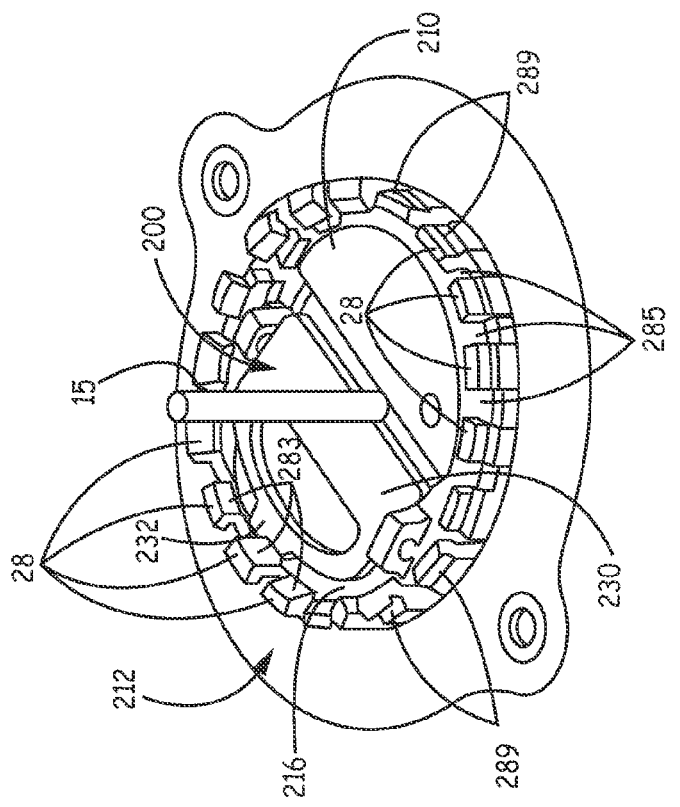
FIG. 2D
FIG. 2E

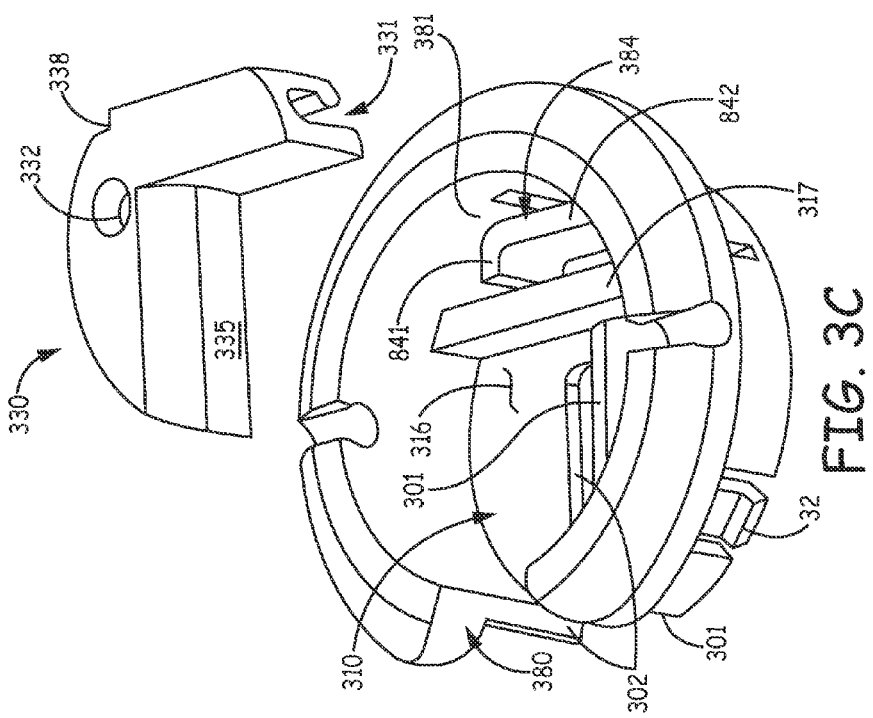
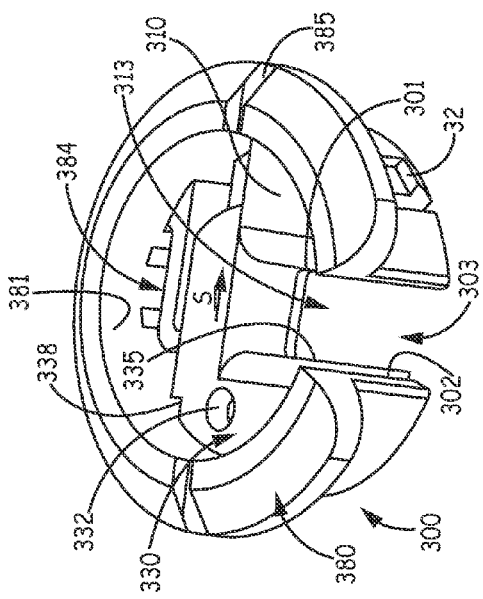
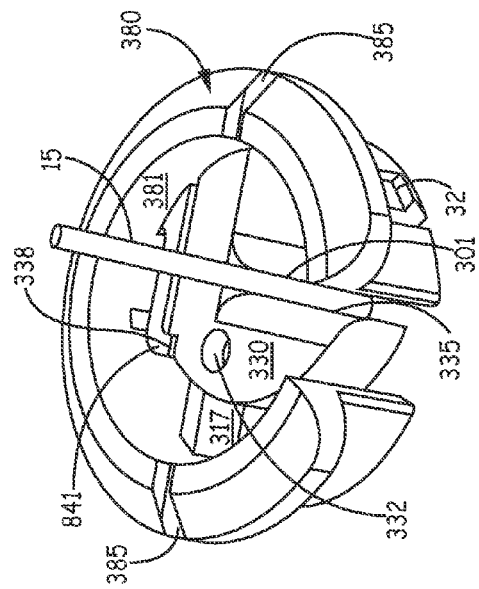

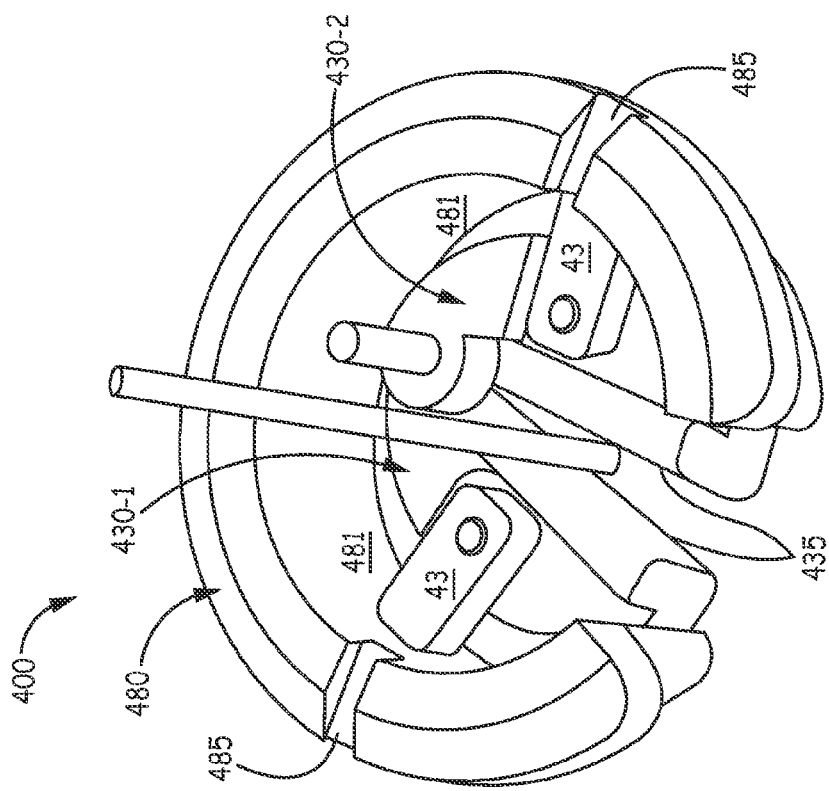
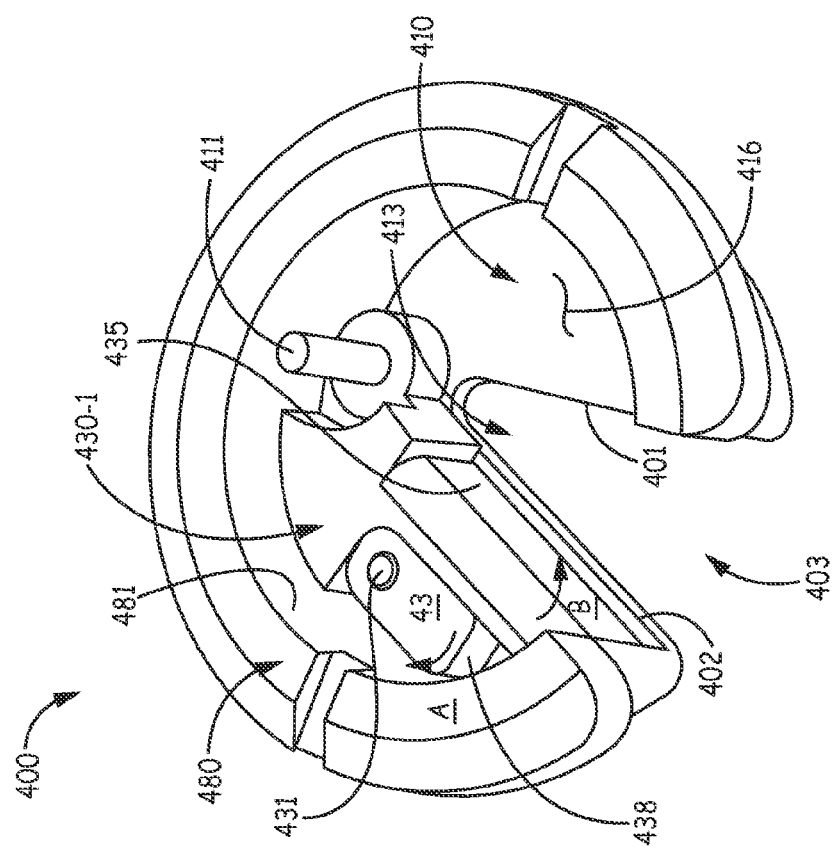
FIG. 4B
FIG. 4A

MEDICAL DEVICE ANCHORING APPARATUS

CROSS-REFERENCE TO RELATED APPLICATIONS

The present application claims priority to U.S. Provisional Patent Application Ser. No. 61/733,584, which was filed on Dec. 5, 2012, and is hereby incorporated by reference in its entirety. The present application is related to the following commonly assigned and co-pending United States Non-provisional Patent Applications, filed concurrently herewith and having the same title as the instant application, each of which is hereby incorporated by reference in its entirety: U.S. patent application Ser. No. 13/795,490; and U.S. patent application Ser. No. 13/795,441.

TECHNICAL FIELD

The present disclosure pertains to medical devices and more particularly to various apparatus, assemblies and methods for anchoring an elongate medical device within a body portal, for example, a burr hole formed in a skull of a patient.

BACKGROUND

Medical procedures for treating a variety of neurological conditions, for example, Parkinson's disease, essential tremor and dystonia, require access to the brain, typically through a burr hole formed in the skull, for the insertion of deep brain stimulating electrodes. Burr holes may also be formed for the insertion of a delivery catheter, for example, to provide drug therapy for similar conditions. Stereotactic apparatus and procedures, which are known to those skilled in the art, may be employed by surgeons to locate inserted electrodes and/or drug delivery ports in target regions of the brain.

FIG. 1A is a perspective view of an exemplary stereotactic guidance system 100 (e.g. Medtronic Nexdrive Micropositioning Drive attached to the Medtronic Nexframe®) mounted to a patient's skull. FIG. 1 illustrates a ring 120 of guidance system 100, which extends around a perimeter of a burr hole 11 formed in the skull, supporting a socket assembly 140 to which a micropositioning drive 160 is attached. Burr hole 11 may be lined with a base ring 112 (FIG. 1B; e.g. the Medtronic Stimloc base) that is mounted around burr hole 11 prior to attaching ring 120 of guidance system 100. FIG. 1 further illustrates an elongate medical device 15, for example, a medical electrical lead carrying one or more stimulating electrodes, held within drive 160 for advancement through burr hole 11 and into the target region of the brain.

FIG. 1B illustrates a portion of the implanted device 15, after guidance system 100 is removed, extending proximally out from base ring 112, which lines burr hole 11, and which is fastened to the skull, for example, via screws received through holes 106 in base ring 112. Those skilled in the art appreciate that a proximal portion of implanted device 15, outside the cranial space, may be routed, beneath the scalp and subcutaneously, to a therapy generator (not shown), for example, implanted in proximity to the clavicle. FIG. 1B further illustrates device 15 extending through a slot of base ring 112 so that device 15 may be secured/anchored between base ring 112 and a cap that snaps into place thereover (not shown; e.g., the Medtronic Stimloc cap). Although various configurations of apparatus for securing elongate medical devices in body portals, such as burr holes, are known in the art, there is still a need for new and improved anchoring apparatus and methods, for example, to increase the ease by which anchoring is activated, without dislodging the implanted device, and without compromising the stability of anchoring.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals/letters denote like elements, and:

FIG. 2D is a perspective view of the assembly of FIGS. 2A-C, which also includes a base ring member, according to some embodiments;

FIG. 2E is a perspective view of the assembly of FIG. 2D over which a cap has been placed, according to some embodiments;

FIGS. 3A-B are perspective views of an anchoring assembly, according to some alternate embodiments;

FIG. 3C is an exploded perspective view of the assembly of FIGS. 3A-B, according to some embodiments;

FIGS. 4A-B are perspective views of an anchoring assembly, according to yet further embodiments.

DETAILED DESCRIPTION

Embodiments of anchoring assemblies disclosed herein are suitable for mounting/fixing in or over a body portal, for example, a cranial burr hole, in order to anchor in place an implanted elongate medical device, such as an electrical lead or a fluid delivery catheter, which is implanted in the body via insertion through the body portal. The assemblies include various configurations of a securing element attached to an upper surface of a plate member in which a slot is formed to receive insertion of the medical device. Each securing element includes an engagement surface and a latching portion, wherein movement of the latching portion of the securing element into engagement with a locking member, which extends from the upper surface of the plate member, moves the engagement surface into a closed position, at which the engagement surface anchors the inserted medical device. Associated methods for employing the various assemblies are disclosed in conjunction with the detailed description of each exemplary embodiment thereof. The following detailed description is exemplary in nature and is not intended to limit the scope, applicability, or configuration of the invention in any way. Rather, the following description provides practical examples, and those skilled in the art will recognize that some of the examples may have suitable alternatives. Examples of constructions, materials, dimensions and fabrication processes are provided for select elements and all other elements employ that which is known by those skilled in the art.

Figures 1A, 1B:
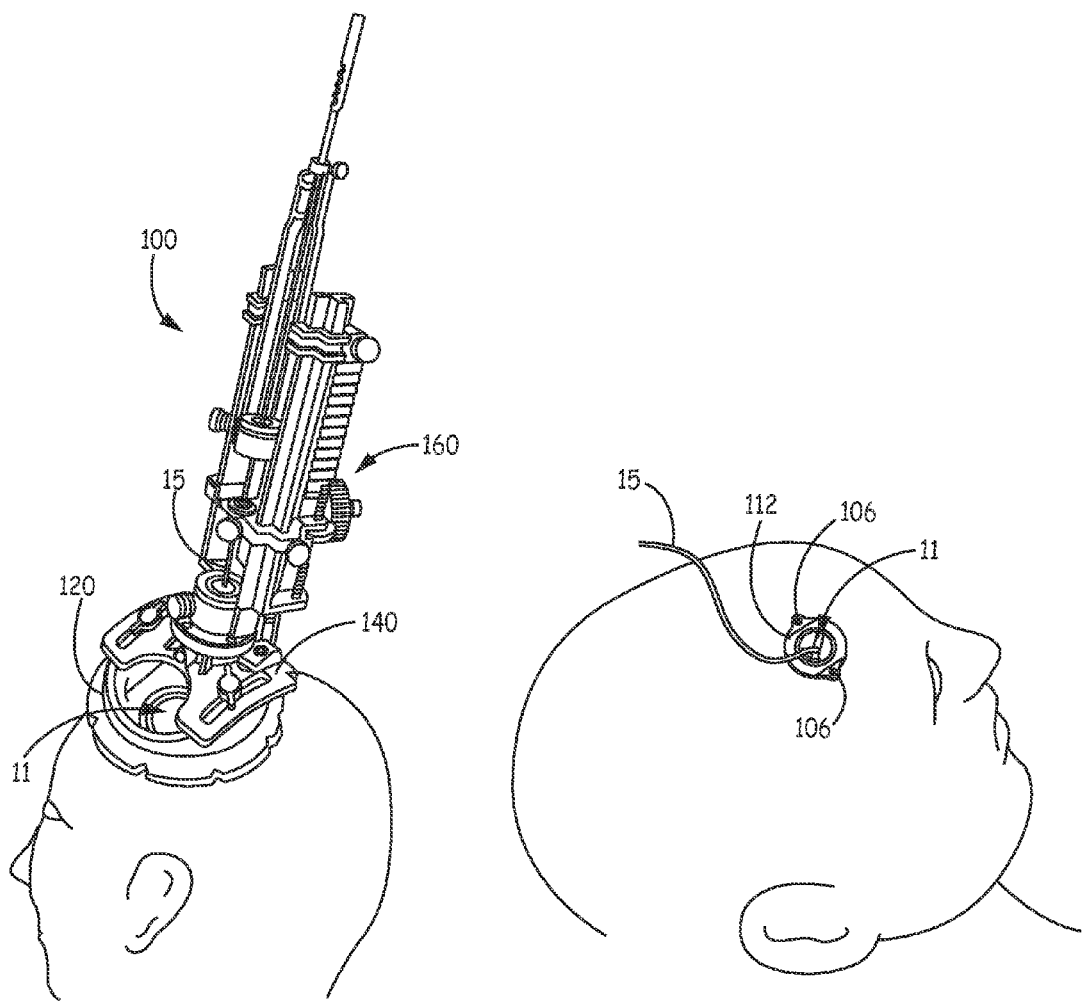
FIG. 1A is a perspective view of an exemplary stereotactic guidance mounted to a patient's skull.
FIG. 1B shows an exemplary base ring mounted in a burr hole of the skull.
Figure 2C:
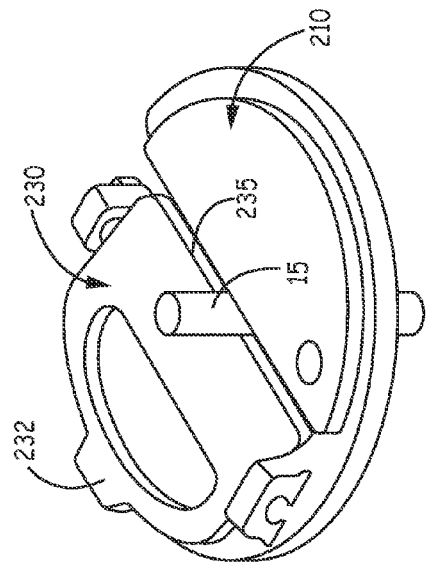
FIG. 2C is another perspective view of the assembly of FIGS. 2A-B, according to some embodiments.
Figure 2A:
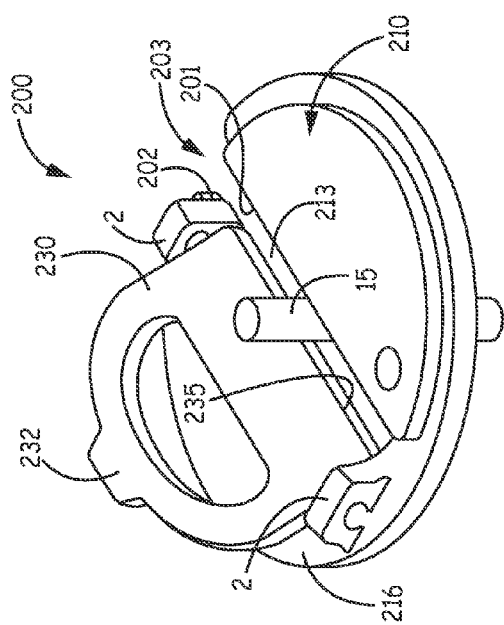
FIGS. 2A-B are perspective views of an anchoring assembly, according to some embodiments.
Figure 2B:
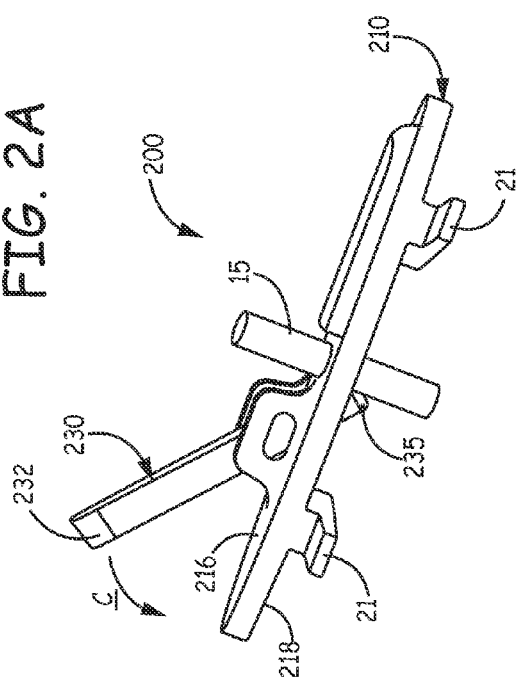

FIGS. 2A-B are perspective views of an anchoring assembly 200, according to some embodiments. FIG. 2A illustrates assembly 200 including a plate member 210, which generally defines a plane, and a securing element 230, which is pivotably attached to an upper surface 216 of plate member 210, for example by mounting features 2, to rotate between an open position at which securing element 230 extends at an angle with respect to the defined plane, and a closed position, at which securing element 230 extends approximately parallel to the defined plane. Assembly 200 may further include a base ring in which plate member 210 is fitted, for example, similar to base ring 112 that lines burr hole 11 (FIG. 1B), or a base ring 212 that is described below in conjunction with FIGS. 2D-E; detent features 21, which are shown extending from a lower surface 218 of plate 210, may engage with an inner perimeter of the base ring to hold assembly 200 in place within the body portal. FIG. 2A further illustrates plate member 210 including a slot 213 having opposing sides 201, 202, which extend generally along the defined plane of plate member 210 from a slot opening 203, at a perimeter of plate member 210. Plate member 210 and securing element 230 may each be formed, for example, by molding, from a biocompatible polymer such as polyurethane, polycarbonate, polysulfone, polyether ether ketone (PEEK), or nylon.

FIGS. 2A-B illustrates securing element 230 in the open position, wherein an engagement surface 235 thereof extends in proximity to side 202 of slot 213 and is spaced apart from first side 201 of slot so that an elongate medical device, for example, a portion of implanted lead 15 that extends proximally out from the body portal, can be inserted into slot 213, via opening 203, for example, prior to fitting assembly 200 into the aforementioned base ring 112, 212. After inserting lead 15 into slot 213, securing element 230 may be rotated toward upper surface 216 of plate 210, per arrow C, to lift engagement surface 235 into the closed position, for example, as shown in FIG. 2C, at which engagement surface 235 is in closer proximity to side 201 of slot 213, and holds lead 15 against first side 201 to anchor lead 15 in the body portal, for example, burr hole 11. According to some embodiments, a groove (not shown) is formed along a length of engagement surface 235, that is, approximately orthogonal to the extent of lead 15 shown in FIGS. 2A-C, for example, to provide a pair of higher pressure gripping areas for holding lead 15 against first side 201 of slot 213. Alternately, or in addition, engagement surface 235 may be roughened or textured, for example, knurled, to enhance gripping. First side 201 of slot 213 may likewise be grooved and/or textured.

With further reference to FIGS. 2A-C, securing element 230 includes a latching portion 232, which may be configured to engage with plate member 210 to secure element 230 in the closed position that is illustrated in FIG. 2C. However, according to some preferred embodiments, a base ring member includes a locking member to engage with and secure element 230 in the closed position. For example, as illustrated in FIG. 2D, base ring 212 (or an insert thereof) includes a locking member formed by one or more detent-like features 28 that extend from upper surface 216 of plate member 210, when plate member 210 is fitted within ring 212; each feature 28 includes an inward-facing cam arm 283 configured to engage latching portion 232 of securing element 230, when securing element 230 is moved into the closed position. FIG. 2D further illustrates each detent-like feature 28 including an outward facing cam arm 289 configured to secure a cap 29, which is shown in FIG. 2E, over assembly 200 and anchored implanted lead 15. Cap 29 may be formed from any of the aforementioned polymer materials (i.e. polyurethane, polycarbonate, polysulfone, PEEK, nylon), or from a relatively low durometer biocompatible polymer, for example, silicone rubber or a lower durometer grade of polyurethane. According to the illustrated embodiment, gaps 285 between adjacent features 285 are sufficient to allow routing of the proximal portion of implanted and anchored lead 15 therethrough for passage through an exit port 295 of cap 29, for example, as illustrated in FIG. 2E. It should be noted that both of engagement surface 235 and first side 201 of slot 213 preferably have rounded edges at upper surface 216 of plate 210 to prevent undue stress concentration on lead 15 when bent over upper surface 216 for routing beneath cap 29.

According to some preferred embodiments, the illustrated plurality of detent-like features 28 are formed in a ring member insert that is separate from a bulk of base ring 212 (that part which includes holes 206 to receive screws/bone fasteners), and the ring member insert is more rigid than the bulk of base ring 212, for example, which may be formed from silicone rubber, or a relatively low durometer polyurethane, or any of the aforementioned polymer materials (i.e. polyurethane, polycarbonate, polysulfone, PEEK, nylon). The ring member insert may be formed, for example, by screw machine manufacture, from a biocompatible metal, such as a stainless steel alloy, or, preferably, nitinol, for MRI compatibility, but may alternately be formed from any of the relatively rigid aforementioned polymer materials.

FIGS. 3A-B are perspective views, and FIG. 3C is an exploded perspective view of an anchoring assembly 300, according to some alternate embodiments. FIGS. 3A-C illustrate assembly 300 including a plate member 310 which generally defines a plane, and a securing element 330, which is attached to an upper surface 316 of plate member 310, for example, via engagement between a grooved mounting feature 331 of securing element 330 and a rail member 317 that protrudes from upper surface 316 of plate member 310. FIGS. 3A-C further illustrate plate member 310 including a slot 313 having opposing sides 301, 302, which extend generally along the defined plane of plate member 310 from a slot opening 303, at a perimeter of plate member 310.

With further reference to FIGS. 3A-B, securing element 330 moves, via sliding engagement with rail member 317, between an open position, which is shown in FIG. 3A, and a closed position, which is shown in FIG. 3B. At the open position, a distance between engagement surface 335 of securing element 330 and first side 301 of slot 313 allows insertion of an elongate medical device, for example, lead 15 into slot 313, via opening 303. After inserting lead 15 into slot 313, securing element 330 may be moved, per arrow S, to the closed position, at which a latching portion 338 of securing element 330 engages with a locking member that secures element 330 in the closed position. FIGS. 3A-C illustrate securing element 330 including a hole, or recess 332 that is configured to receive a tool for moving element 330 between the open and closed positions, according to some embodiments and methods. FIGS. 3A-B further illustrate the locking member being formed by a portion of a ring member 380 of assembly 300, the portion being a flexible detent member 384 that extends from an inner surface 381 of ring member 380. With reference to FIG. 3C, ring member 380 is shown extending from upper surface 316 of plate member 310 and about the perimeter of plate member 310, from first side 301 of slot 313 to second side 302 of slot 313; and detent member 384 is shown including an arm portion 842 terminated by an interlocking tip 841. According to the illustrated embodiment, detent member 384 is biased away from inner surface 381 of ring member 380 and is held against the bias by securing member 330, until securing member 330 is moved, per arrow S, into the closed position (FIG. 3b), at which latching portion 338 of member 330, which is in the form of an interlocking recess, is located to receive interlocking tip 841 of detent member 384 in interlocking engagement.

Like plate member 210 and securing element 230, plate member 310, securing element 330, and ring member 380 may each be formed, for example, by molding, from a biocompatible polymer such as polyurethane, polycarbonate, polysulfone, polyether ether ketone (PEEK), or nylon. Furthermore, according to some embodiments, engagement surface 335, like engagement surface 235, includes the above-described groove formed along a length thereof. Alternately, or in addition, engagement surface 335 may be roughened or textured, for example, knurled, to enhance gripping, as may first side 301 of slot 313. FIGS. 3A-C illustrate ring member 380 integrally formed with plate member 310, and assembly 300 including detent features 32 configured to engage with a base ring, such as base ring 112 described above; yet, according to alternate embodiments, ring member 380 may be configured as a separate base ring, which, when lining a body portal, may receive plate member 310 and attached securing element 330 (in the open position) fitted therein, as lead 15 is inserted into slot 313. With further reference to FIG. 3B, after fitting assembly 300 into a base ring and anchoring lead 15, a proximally extending portion of lead 15 may be routed through one of grooves 385 formed in ring member 380, and a cap, for example, similar to cap 29 shown in FIG. 2E, may be attached over plate member 310, ring member 380, and routed lead 15.

FIGS. 4A-B are perspective views of an anchoring assembly 400, according to yet further embodiments. FIG. 4A illustrates assembly 400 including a plate member 410 which generally defines a plane, and a securing element 430-1, which is pivotably attached to an upper surface 416 of plate member 410, for example, via a post 411 of plate member 410, so that element 430-1 rotates approximately parallel to the defined plane. FIG. 4A further illustrates plate member 410 including a slot 413 having opposing sides 401, 402, which extend generally along the defined plane of plate member 410 from a slot opening 403, at a perimeter of plate member 410. FIG. 4A shows securing element 430-1 in an open position, wherein an engaging surface 435 thereof extends adjacent side 402 of slot 413 and is spaced apart from side 401 of slot 413, so that an elongate implanted device, such a lead 15, may be inserted into slot 413, via opening 403. According to some embodiments, in which assembly 400 includes a single securing element 430-1, after the device is inserted into slot 413, securing element 430-1 is rotated, per arrow B, to move engagement surface 435 closer to side 401 of slot 413, where engagement surface 435 anchors the device against side 401. However, with reference to FIG. 4B, assembly 400 may include a pair of securing elements 430-1, 430-2, both pivotably attached, via post 411, to plate member 410, wherein engagement surfaces 435 thereof face one another. FIG. 4B illustrates securing elements 430-1, 430-2 having been rotated toward one another into a closed position, at which lead 15 is anchored between engagement surfaces 435 thereof.

With further reference to FIGS. 4A-B, each securing element 430-1, 430-2 includes a latching portion formed by a cam member 43 pivotably mounted thereon, via a post 431 of securing element 430-1, 430-2. FIGS. 4A-B further illustrate assembly 400 including a ring member 480 that extends from upper surface 416 of plate member 410 and about the perimeter of plate member 410, from first side 401 to second side 402 of slot 413. Each cam member 43 is shown including a contact surface 438, which is located within a perimeter of the corresponding securing element 430-1, 430-2, when the securing element is in the open position (FIG. 4A). Ring member 480 acts as a locking member for assembly 400, such that, when each cam member 43 is rotated per arrow A, contact surface 438 is moved to a location outside the corresponding securing element perimeter, to engage with an inner perimeter surface 481 of ring member 480, thereby moving the corresponding securing element 430-1, 430-2 into the closed position (FIG. 4B); and, when each latching portion/cam member 43 is moved into engagement with inner surface 481 of ring member 480, the corresponding securing element 430-1, 430-2 is moved into the closed position and secured thereat by the engagement.

FIGS. 4A-B illustrate ring member 480 and plate member 410 integrally formed, for example, by molding biocompatible polymer such as polyurethane, polycarbonate, polysulfone, polyether ether ketone (PEEK), or nylon. Securing elements 430-1, 430-2 (including cam members 43) may also be molded parts formed from any of these polymer materials. Engagement surfaces 435 may include the above-described groove formed along lengths thereof, and/or may be roughened or textured, for example, knurled, to enhance gripping, as may side 401 of slot 413, for the embodiment including the single securing element 430-1. Although not shown, ring member 480 includes detent features (similar to features 32 of ring member 380) that are configured to engage with a base ring, such as base ring 112 described above; yet, according to alternate embodiments, ring member 480 may be configured as a separate base ring, which when lining a body portal, may receive plate member 410 and attached securing element(s) 430-1, 430-2 (in the open position) fitted therein, as lead 15 is inserted into slot 413. With further reference to FIG. 4B, after fitting assembly 400 into a base ring and anchoring lead 15, a proximal extending portion of lead 15 may be routed through one of grooves 485 formed in ring member 480, and a cap, for example, similar to cap 29 shown in FIG. 2E, may be attached over plate member 410, ring member 480, and routed lead 15.

Figure 5B:
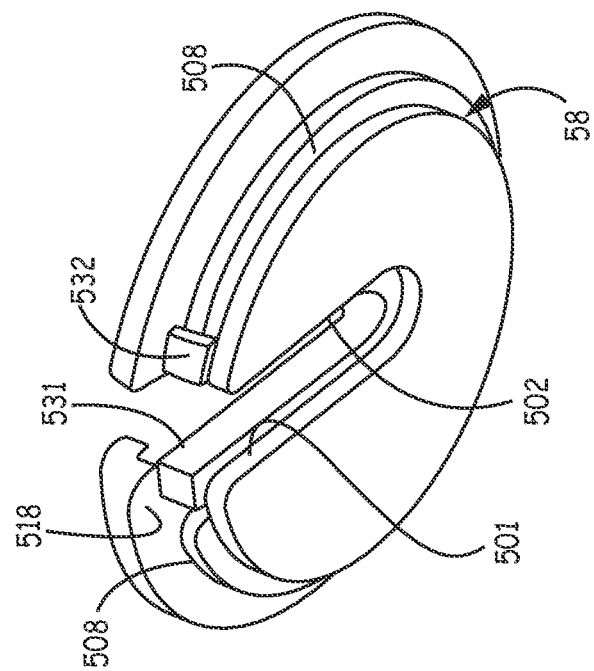
FIGS. 5A-B are perspective views of an anchoring assembly, according to some additional embodiments.
Figure 5A:
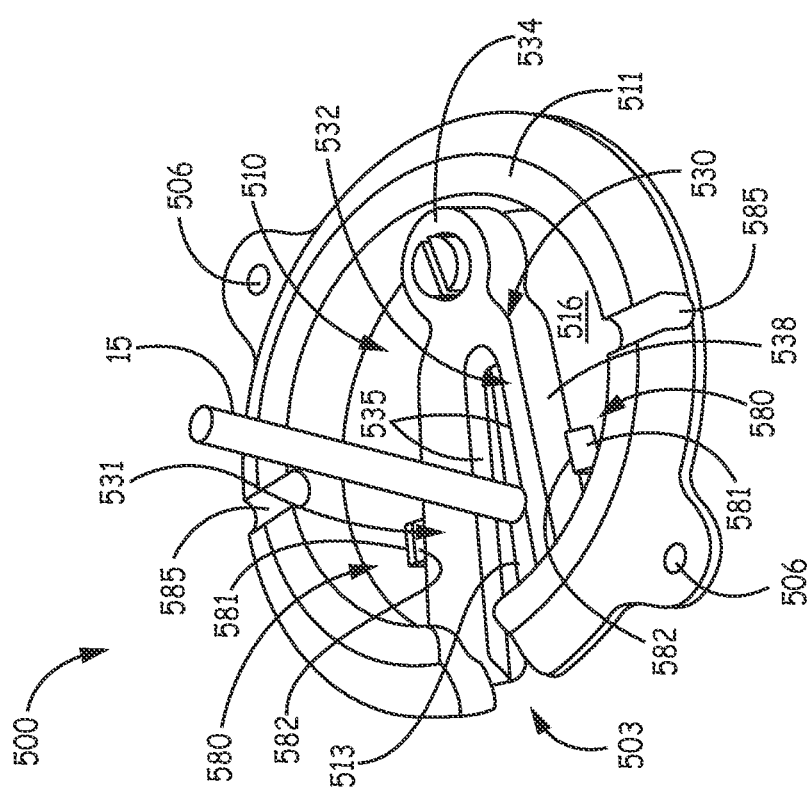

FIGS. 5A-B are perspective views of an anchoring assembly 500, according to some additional embodiments. FIGS. 5A-B illustrate assembly 500 including a plate member 510, generally defining a plane, and a pair of opposing securing elements 531, 532 in the form of arms of a spring clip 530 mounted on an upper surface 516 of plate member 510. FIGS. 5A-B further illustrate plate member 510 including a slot 513 having opposing sides 501, 502, which extend generally along the defined plane of plate member 510 from a slot opening 503, at a perimeter of plate member 510. Securing elements 531, 532 of spring clip 530 are shown joined at an end 534 which is press fit around a post that protrudes from upper surface 516 of plate 510, according to some embodiments, wherein each element 531, 532 extends alongside a corresponding side 501, 502 of slot 513. Plate member 510 and spring clip 530 may be formed, for example, by molding, from a biocompatible polymer such as polyurethane, polycarbonate, polysulfone, PEEK, or nylon; alternately, spring clip 530 may be formed from any suitable elastic material, such as stainless steel, or nitinol, to provide an elasticity with enhanced creep resistance, for example, to prevent significant loss of spring force over time.

FIG. 5A shows securing elements 531, 532 in a closed position at which engagement surfaces 535 thereof engage lead 15 therebetween for anchoring. According to the illustrated embodiment, securing elements 531, 532 are spring biased away from one another so that in the closed position, a locking member, which is in the form of a pair of ramped protrusions 580, holds securing elements 531, 532 together in the closed position, against the spring bias thereof, by engaging latching portions thereof, which are outward facing sides 538. Protrusions 580 extend from upper surface 516 of plate member 510, and are preferably integrally formed therewith. Although not shown, it should be understood that each securing element 531, 532, when in an open position, extends on an outer, ramped surface 581 of each protrusion 580, so that an implanted elongate device, for example, lead 15, may be inserted into slot 513, via opening 503. Once the device is inserted into slot 513, a plug portion 58 (FIG. 5B), which extends from a lower surface of plate member 510 (opposite upper surface 516) and includes a press fit flange 508, is radially compressed within a hole/body portal, and then spring clip securing elements 531, 532 are closed, or forced together, for example, with surgical forceps, against the spring bias thereof. Securing elements 531, 532 are retained in the closed position by opposing cliff walls 582 of locking member/ramped protrusions 580, which engage outward facing sides/latching portions 538 of securing elements 531, 532.

With further reference to FIG. 5A, after anchoring lead 15, the proximal extending portion thereof may be routed through one of grooves 585 formed in an outer perimeter ridge 511 that protrudes from upper surface 516 of plate member 510, and a cap, for example, similar to cap 29 shown in FIG. 2E, may be attached over plate member 510 and routed lead 15. Plate member 510 preferably includes holes 506 through which screws may be inserted for fastening anchoring assembly 500 to a skull after press-fitting assembly 500 into a body portal thereof.

In the foregoing detailed description, the invention has been described with reference to specific embodiments and methods. However, it may be appreciated that various modifications and changes can be made without departing from the scope of the invention as set forth in the appended claims.

The invention claimed is:

1. An anchoring assembly for an elongate medical device, the assembly comprising:
   a plate member generally defining a plane and including a slot that extends generally along the plane, the slot including a first side, a second side opposite the first side, and a slot opening, located at a perimeter of the plate member, from which the first and second sides extend;
   a locking member extending from an upper surface of the plate member, wherein the locking member comprises a ring member extending about the perimeter of the plate member; and
   a securing element attached to the upper surface of the plate member and being moveable relative to the plate member between an open position and a closed position, the securing element including an engagement surface and a latching portion, the latching portion being configured to engage the locking member, the engagement surface being spaced apart from the first side of the slot by a first distance at the open position, and the engagement surface being spaced apart from the first side of the slot by a second distance at the closed position, the first distance allowing insertion of the elongate medical device, through the slot opening and between the engagement surface and the first side of the slot, and the second distance being less than the first distance, and at which the engagement surface anchors the medical device;
   wherein, when the latching portion of the securing element is moved into engagement with the locking member, the securing element is moved into the closed position; and
   the securing element is secured in the closed position by the engagement between the latching portion thereof and the locking member.

2. The assembly of claim 1, wherein the securing element is pivotably attached to the plate member so that the securing element extends at an angle with respect to the plane in the open position, and the securing element extends generally parallel to the plane in the closed position.

3. The assembly of claim 1, wherein the ring member comprises a separate base ring or base ring insert into which the plate member is fitted, and the ring member includes at least one detent-like feature with which the latching portion is configured to engage.

4. The assembly of claim 3, wherein the at least one detent-like feature of the ring member comprises a plurality of detent-like features spaced apart from one another about a circumference of the ring member.

5. The assembly of claim 4, wherein a gap between a pair of adjacent spaced apart detent-like features of the ring member allows routing of a proximal portion of the medical device therebetween.

6. The assembly of claim 4, further comprising a cap configured to cover the plate member and the securing element in the closed position; and wherein each of the plurality of detent-like features of the ring member are further configured to engage with the cap when the cap covers the plate member and the securing element in the closed position.

7. The assembly of claim 4, wherein the securing element is pivotably attached to the plate member so that the securing element extends at an angle with respect to the plane in the open position, and the securing element extends generally parallel to the plane in the closed position.

8. An anchoring assembly for an elongate medical device, the assembly comprising:
   a plate member generally defining a plane and including a slot that extends generally along the plane, the slot including a first side, a second side opposite the first side, and a slot opening, located at a perimeter of the plate member, from which the first and second sides extend;
   a securing element attached to the plate member and including an engagement surface and a latching portion, the securing element being pivotable relative to the plate member from an open position, at which the securing element extends at an angle with respect to the plane, to a closed position, at which the securing element extends generally parallel to the plane, and at which the latching portion is engaged, the engagement surface being spaced apart from the first side of the slot by a first distance at the open position, and the engagement surface being spaced apart from the first side of the slot by a second distance at the closed position, the first distance allowing insertion of the elongate medical device, through the slot opening and between the engagement surface and the first side of the slot, and the second distance being such that the engagement surface presses the medical device against the first side of the slot to anchor the medical device between the first side and the engagement surface; and a ring member sized to fit around the perimeter of the plate member, the ring member including at least one detent-like feature with which the latching portion is configured to engage.

9. The assembly of claim 8, wherein the engagement surface is located below the plane in the open position and rises to the plane when the securing element is pivoted to the closed position.

10. The assembly of claim 8, wherein the ring member comprises a separate base ring or base ring insert, and the at least one detent-like feature of the ring member comprises a plurality of detent-like features spaced apart from one another about a circumference of the ring member.

11. The assembly of claim 10, wherein a gap between a pair of adjacent spaced apart detent-like features of the ring member allows routing of a proximal portion of the medical device therebetween.

12. The assembly of claim 10, further comprising a cap configured to cover the plate member and the securing element in the closed position; and wherein each of the plurality of detent-like features of the ring member are further configured to engage with the cap when the cap covers the plate member and the securing element in the closed position.

* * * * *